United States Patent [19]

Satzinger et al.

[11] Patent Number: 4,584,374

[45] Date of Patent: Apr. 22, 1986

[54] 4-THIOXO-BENZOPYRANO[2,3-D]PYRIMIDINE DERIVATIVES

[75] Inventors: Gerhard Satzinger, Denzlingen; Hubert Barth, Emmendingen; Johannes Hartenstein, Stegen-Wittental; Manfred Herrmann; Edgar Fritschi, both of St. Peter; Ilse-Dore Schütt, Glottertal, all of Fed. Rep. of Germany

[73] Assignee: Warner-Lambert Company, Morris Plains, N.J.

[21] Appl. No.: 653,185

[22] Filed: Sep. 24, 1984

[30] Foreign Application Priority Data

Sep. 30, 1983 [DE] Fed. Rep. of Germany ....... 3335473

[51] Int. Cl.$^4$ ............... C07D 491/052; C07D 491/153
[52] U.S. Cl. ..................................... 544/247; 544/115; 544/250
[58] Field of Search ....................... 544/250, 246, 247; 514/232, 257, 267

[56] References Cited

U.S. PATENT DOCUMENTS

| | | | |
|---|---|---|---|
| 3,272,811 | 9/1966 | Ohnacker et al. | 544/278 X |
| 3,468,888 | 9/1969 | Chow | 544/250 |
| 3,578,666 | 5/1971 | Manning | 544/278 X |
| 3,772,230 | 11/1973 | Hardtmann | 544/282 |
| 4,272,535 | 9/1981 | Blythin | 544/115 X |
| 4,297,355 | 10/1981 | Blythin | 544/115 X |

OTHER PUBLICATIONS

O'Callaghan, Chemical Abstracts, vol. 93, 220682j (1980).
O'Callaghan et al., Chemical Abstracts, vol. 100, 103286k (1984).

*Primary Examiner*—Donald G. Daus
*Assistant Examiner*—Diana G. Rivers
*Attorney, Agent, or Firm*—Ronald A. Daignault

[57] ABSTRACT

4-Thioxobenzopyrano[2,3-d]-pyrimidine derivatives of the general formulae Ia or Ib

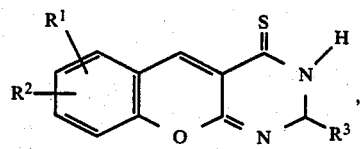

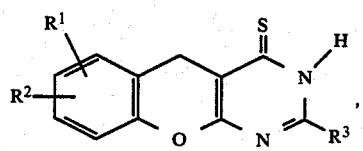

are described.

Compounds Ia and Ib are tautomers and are valuable intermediates for the preparation of 5H-[1]-benzopyrano[2,3-d]pyrimidine derivatives having ulcer-protective action without inhibition of secretion.

3 Claims, No Drawings

4-THIOXO-BENZOPYRANO[2,3-D]PYRIMIDINE DERIVATIVES

SUMMARY OF THE INVENTION

The present invention relates to 4-thioxo-benzopyrano[2,3-d]pyrimidine derivatives of the formulae Ia or Ib

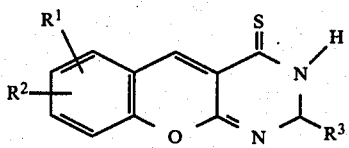

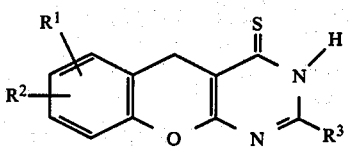

in which $R^1$ and $R^2$, which may be the same or different, represent a hydrogen or halogen atom, a hydroxyl group or a straight-chain or branched alkoxy group with up to four carbon atoms or together represent an alkylenoxy- or alkylendioxy-group with up to three carbon atoms or a condensed aromatic ring, and $R^3$ represents a phenyl radical which may be substituted.

DETAILED DESCRIPTION

The compounds Ia and Ib are tautomers.

As aromatic ring $R^1$ and $R^2$, there is included, for example, the phenyl ring. Preference is accorded to the ubsubstituted phenyl ring in 6,7 position.

As halogen atoms fluorine, chlorine, bromine, and iodine atoms are included. Preference is accorded to the bromine atom.

As an alkylenoxy group an ethyleneoxy group forming an oxolene ring is preferred. As an alkylenedioxy group a methylenedioxy group forming a 1,3-dioxolene ring is preferred.

As substituents of the phenyl radical $R^3$ come into consideration one to three substituents out of the group of the halogen atoms, dialkylamino groups with up to four carbon atoms or alkyl or alkoxy groups with up to four carbon atoms as well as up to two akylenedioxy groups with up to two carbon atoms.

Preference is accorded to compounds of the general formulae Ia or Ib, in which $R^1$ and $R^2$, which may be the same or different, represent a hydrogen or bromine atom, a hydroxyl, methoxy, or ethoxy group or together an unsubstituted benzene ring condensed in the 6,7 position, and $R^3$ represents an unsubstituted phenyl radical, which may also be substituted by a halogen atom, a dimethylamino, a methyl or methylenedioxy group or by up to three methoxy groups.

Particular preference is accorded to compounds of the general formulae Ia or Ib, in which the radicals $R^1$ and $R^2$ are the same or different, and represent a hydrogen or bromine atom or a methoxy group, and $R^3$ represents a phenyl, 4-dimethylaminophenyl, 4-methoxyphenyl, 4-hydroxyphenyl, or 4-methylphenyl radical.

Another subject matter of the invention is a process to prepare the compounds of the general formulae Ia and Ib, characterized by that in a generally known manner a compound of the general formula II

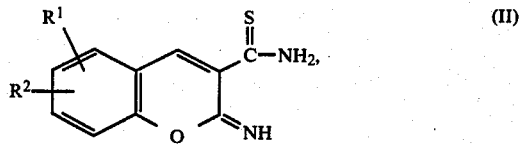

in which $R^1$ and $R^2$ have the above meanings, is reacted with an aromatic aldehyde of the general formula III

in which $R^3$ has the above meaning, in the presence of a catalytic amount of a base, preferably at reflux temperature, and subsequently is tautomerized with a strong base, if desired.

Particularly satisfactory as bases for the catalytic reaction proved piperidine and triethylamine. The water forming during the reaction is best removed azeoptropically by using a solvent immiscible with water, such as e.g., methylenechloride, chloroform, benzene, or toluene as an extracting medium.

As a rule the reaction time lasts between 6 and 20 hours.

The compounds of the general formula Ia, mostly colored yellow to orange, usually are precipitated in the course of the reaction and may be isolated by filtration, washed and dried, or they are isolated from the residue following removal of the solvent.

The starting products of the general formula II are obtained according to DE-OS No. 28 01 353 by well known processes reacting o-hydroxy-benzaldehyde derivatives with 2-cyano-thioacetamide.

The compounds of the general formula Ia and Ib are valuable intermediate products in the preparation of 5H-[1]-benzopyrano-[2,3-d]-pyrimidine derivatives of the general formula IV

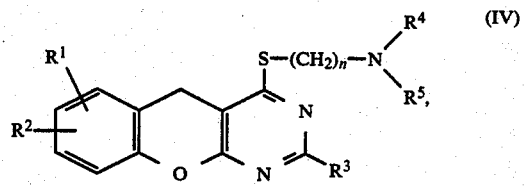

in which the radicals $R^1$, $R^2$, and $R^3$ have the above meanings, and $R^4$ and $R^5$, which may be the same of different, represent a hydrogen atom, a straight-chain or branched alkyl group with up to six carbon atoms, or together with the nitrogen atom a saturated five- or six-membered ring with further hetero-atoms, if necessary, and n represents the Figures 2 or 3.

The compounds of the formula IV have been described in detail in U.S. application Ser. No. 653,175, filed Sept. 24, 1984 and represent pharmaceutical agents with an extraordinary ulcerprotective mode of action without any antisecrectory component.

The preparation of compounds IV from the compounds Ia and Ib is made by tautomerizing a compound of the general formula Ia with a strong base in an organic solvent and by reacting the obtained compound of the general formula Ib

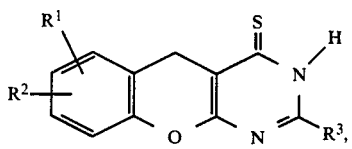

in which the radicals $R^1$, $R^2$, and $R^3$ have the above meanings, if necessary without isolation, with an alkylation agent of the general formula V

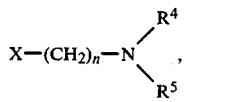

in which the radicals $R^4$ and $R^5$ and n have the above meanings and X represents a reactive ester group.

This reaction is preferable carried out with polar solvents, such as e.g., lower alkanols. At increased temperature the reaction lasts up to six hours.

As bases come into consideration, e.g., potassium carbonate, potassium hydroxide, sodium methanolate or sodium ethanolate.

The following examples serve to further illustrate the invention:

EXAMPLE 1

(tautomeric form Ia)

2,3-Dihydro-2-phenyl-4-thioxo-[1]-benzopyrano[2,3-d]pyrimidine

Under a separator 10 g 2-imino-3-thiocarbamoyl(2H) chromene, 5.2 g benzaldehyde, and 5 drops piperidine in 1 l benzene are boiled for six hours. After cooling the yellow product of the reaction which has precipitated, is sucked off, washed with a small amount of benzene, and dried under a vacuum. Yield 11.0 g, yellow crystals, m.p. 220° C. (decomp.).

In analogous manner are obtained:

2-(4-chlorophenyl)-2,3-dihydro-4-thioxo-[1]-benzopyrano[2,3-d]pyrimidine

Yield 61%, yellow crystals, m.p. 246° C. (decomp.).

2-(4-dimethylaminophenyl)-2,3-dihydro-4-thioxo-[1]-benzopyrano[2,3-d]pyrimidine

Yield 63%, orange-colored crystals, m.p. 218° C. (decomp.).

2,3-dihydro-2-(4-hydroxyphenyl)-4-thioxo-[1]-benzopyrano[2,3-d]pyrimidine

Yield 80%, yellow crystals, m.. 248° C. (decomp.).
2,3-dihydro-2-(4-methylphenyl)4-thioxo-[1]-benzopyrano[2,3-d]pyrimidine Yield 52%, yellow crystals, m.p. 205° C. (decomp.).

2,3-dihydro-2-(4-methoxyphenyl)-4-thioxo-[1]benzopyrano[2,3-d]pyrimidine

Yield 52%, yellow crystals, m.p. 202° C. (decomp.).

2,3-dihydro-2-(3,4-methylenedioxyphenyl)-4-thioxo-[1]-benzopyrano[2,3-d]pyrimidine Yield 56%, yellow crystals, m.p. 226° C. (decomp.).

2,3-dihydro-2-(3,4,5-trimethoxyphenyl)-4-thioxo-[1]-benzopyrano[2,3-d]pyrimidine Yield 85%, yellow crystals, m.p. 290° C. (decomp.).

2,3-dihydro-7-methoxy-2-phenyl-4-thioxo-[1]-benzopyrano[2,3-d]pyrimidine

Yield 87%, yellow crystals, m.p. 223° C. (decomp.).

9,10-dihydro-9-phenyl-11-thioxo-naphtho[1',2':5,6]-pyrano[2,3-d]pyrimidine

Yield 85%, m.p. 320° C. (decomp.).

7-bromo-2,3-dihydro-2-phenyl-4-thioxo-[1]-benzopyrano[2,3-d]pyrimidine

Yield 80%, m.p. 330° C. (decomp.).

9-ethoxy-2,3-dihydro-2-phenyl-4-thioxo-[1]-benzopyrano[2,3-d] pyrimidine

Yield 77%, m.p. 215° C. (decomp.).

2,3-dihydro-6,8-dimethoxy-2-phenyl-4-thioxo-[1]-benzopyrano[2,3-d]pyrimidine

Yield 68%, m.p. 298° C. (decomp.).

2,3-dihydro-7-methoxy-2-(4-methoxyphenyl)-4-thioxo[1]-benzopyrano[2,3-d]pyrimidine Yield 72%, m.p. 250° C. (decomp.).

7-brom-2,3-dihydro-2-(4-methoxyphenyl)-4-thioxo-[1]-benzopyrano[2,3-d]pyrimidine Yield 75%, m.p. 235° C. (decomp.).

2,3-dihydro-7,8-methylenedioxy-2-(3,4-methylenedioxyphenyl)-4-thioxo-[1]-benzopyrano[2,3-d]pyrimidine Yield 93%, yellow crystals; m.p. 270° C. (decomp.).

2,3,7,8-tetrahydro-8-(4-methylphenyl)-6-thioxofuro[2',3':7,8][1]benzopyrano[2,3-d]pyrimidine Yield 80%, yellow crystals; m.p.>210° C. (decomp.).

EXAMPLE 2

(tautomeric form Ib)

2-Phenyl-4-thioxo-3H,5H-[1]-benzopryano[2,3-d]pyrimidine 1.1 g sodium are disolved in 300 ml abs. ethanol. After adding 14.6 g 2,3-dihydro-2-phenyl-4-thioxo[1]-benzopyrano[2,3-d]pyrimidine the mixture is heated to boiling for one hour. Subsequently the reaction mixture is concentrated in a rotary evaporator, poured into 300 ml water and cautiously acidified with diluted hydrochloric acid. The precipitate is collected on a filter and recrystallized from dimethylformamide/ethanol.

Yield 80%, yellow crystals, m.p. 245° C. (decomp.).
In analogous manner there are obtained:

2-(4-dimethylaminophenyl)-4-thioxo-3H,5H-[1]-benzopyrano[2,3-d]pyrimidine

Yield 76%, yellow crystals, m.p. 245° C. (decomp.).

2-(4-methoxyphenyl)-4-thioxo-3H,5H-[1]-benzopyrano[2,3-d]pyrimidine

Yield 74%, yellow crystals, m.p. 265° C. (decomp.).

2-(4-chlorophenyl)-4-thioxo-3H,5H-[1]-benzopyrano[2,3-d]pyrimidine

Yield 70%, yellow crystals, m.p. 340° C. (decomp.).

4-thioxo-2-(3,4,5-trimethoxyphenyl)-3H,5H-[1]-benzopyrano[2,3-d]pyrimidine

Yield 79%, ochre-colored crystals, m.p. 290° C. (decomp.).

2-(4-hydroxyphenyl)-4-thioxo-3H,5H-[1]-benzopyrano[2,3-d]pyrimidine

Yield 65%, yellowish crystals, m.p. 274° C. (decomp.).

We claim:

1. A 4-thioxo-benzopyrano[2,3-d]-pyrimidine derivative of the Formulae Ia or Ib

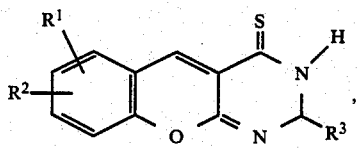

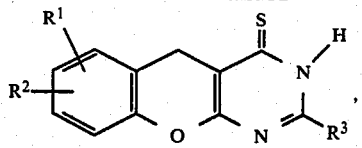

in which $R^1$ and $R^2$, which may be the same or different, represent a hydrogen or halogen atom, a hydroxyl group or a straight-chain or branched alkoxy group with up to four carbon atoms or together represent an alkylenoxy- or alkylendioxy-group with up to three carbon atoms or, together an unsubstituted benzene ring condensed in the 6,7-positions and $R^3$ a phenyl radical or phenyl substituted by a halogen atom, a dimethylamino, a methyl or methylenedioxy group or by up to three methoxy groups.

2. A compound according to claim 1, where in $R^1$ and $R^2$ are the same or different and represent a hydrogen or bromine atom, a hydroxyl, methoxy, or ethoxy group or together an unsubstituted benzene ring condensed in the 6,7-positions, and $R^3$ represents a phenyl radical or phenyl substituted by a halogen atom, a dimethylamino, a methyl or methylenedioxy group or by up to three methoxy groups.

3. A compound according to claim 1, wherein $R^1$ and $R^2$ are the same or different and represent a hydrogen or bromine atom or a methoxy group and $R^3$ represents phenyl, 4-dimethylaminophenyl, 4-methoxyphenyl, 4-hydroxyphenyl, or 4-methylphenyl.

* * * * *